United States Patent [19]

Stellwag et al.

[11] Patent Number: 4,771,003

[45] Date of Patent: Sep. 13, 1988

[54] HEAT STABLE ALKALINE PROTEASES PRODUCED BY A BACILLUS

[75] Inventors: Edmund J. Stellwag, Damascus; Donald R. Durham, Gaithersburg; Wayne E. Swann, Columbia; Carol A. Nolf, Silver Spring, all of Md.; David B. Stewart, Arlington, Va.

[73] Assignee: Genex Corporation, Gaithersburg, Md.

[21] Appl. No.: 790,256

[22] Filed: Oct. 22, 1985

[51] Int. Cl.$^4$ .......................... C12N 9/54; C12N 1/20; C12R 1/07

[52] U.S. Cl. .................................... 435/221; 435/253; 435/832; 252/174.12; 252/DIG. 12

[58] Field of Search .................................. 435/220–222, 435/253; 252/174.12, DIG. 12

[56] References Cited

U.S. PATENT DOCUMENTS

| 3,655,513 | 4/1972 | Sternberg. | |
|---|---|---|---|
| 3,723,250 | 3/1973 | Aunstrup et al. | |
| 3,790,482 | 2/1974 | Jones et al. | 252/525 |
| 3,827,938 | 8/1974 | Aunstrup et al. | |
| 3,855,064 | 12/1974 | Vroemen. | |
| 3,871,963 | 3/1975 | Tobe et al. | |
| 3,931,034 | 1/1976 | Inamorato et al. | 252/132 |
| 4,052,262 | 10/1977 | Horikoshi et al. | 435/221 |
| 4,252,663 | 2/1981 | Eriksson | 252/99 |
| 4,287,101 | 9/1981 | Nishio et al. | 252/537 |
| 4,429,044 | 1/1984 | Boguslawski et al. | 435/220 |
| 4,480,037 | 10/1984 | Ichishima et al. | 435/221 |
| 4,529,525 | 7/1985 | Dormal et al. | 252/132 |

FOREIGN PATENT DOCUMENTS 1240058 7/1971 United Kingdom.
1247292 9/1971 United Kingdom.

OTHER PUBLICATIONS

Chemical Abstract, 100:33279j.
Chemical Abstract, 80:144405k.

Primary Examiner—Lionel M. Shapiro
Attorney, Agent, or Firm—Saidman, Sterne, Kessler & Goldstein

[57] ABSTRACT

Novel enzymes exhibiting proteolytic activity in alkaline media and stability at high temperatures and under alkaline conditions are produced by a novel Bacillus strain designated GX6638 or its mutants or variants. These enzymes are especially well-suited for inclusion in washing compositions. A culture of GX6638 has been deposited with the American Type Culture Collection, Rockville, Md. as ATCC No. 53278.

14 Claims, No Drawings

HEAT STABLE ALKALINE PROTEASES PRODUCED BY A BACILLUS

TECHNICAL FIELD

The present invention relates to proteolytic enzymes produced by a novel strain of Bacillus and characterized by activity in alkaline media and stability at high temperatures and under highly alkaline conditions. The enzyme is useful in washing compositions.

BACKGROUND OF THE INVENTION

Enzymes having proteolytic activity at alkaline pH are known and have been described in several references, such as U.S. Pat. Nos. 3,674,643 and 4,002,572. Proteolytic enzymes produced by cultivation of members of the genus Bacillus constitute the major source of proteolytic enzymes used in detergent washing compositions. Classified generically as serine proteases, these proteolytic enzymes generally are characterized by sensitivity to diisopropylphosphofluoridate and phenylmethylsulfonyl fluoride, resistance to thiol reagents and metal chelators, molecular weights ranging from about 20,000 to about 28,000 daltons, and isoelectric points in the alkaline range. As detergent additives, it is also important for the proper functioning of these enzymes that they be active in solutions at alkaline pH values and in the presence of sequestering agents, surfactants, and in some cases, oxidizing agents.

Furthermore, for an enzyme to be useful in a detergent composition it advantageously exhibits long term stability in the detergent product. Traditionally, this has proved difficult to achieve, at least for liquid detergent formulations. Frequently, proteolytic enzymes lose their activity in aqueous media during storage. Several recent U.S. patents, such as U.S. Pat. Nos. 4,111,855, issued to Barrat et al., and 4,318,818, issued to Letton et al., have disclosed means for stabilizing proteolytic enzymes in aqueous-based detergent compositions through the addition of certain specific compounds to the detergent formulations. Further improvements in this area are, however, sought.

Accordingly, it is an object of the present invention to provide a group of novel proteolytic enzymes which exhibit good stability under alkaline conditions. It is also an object of the invention to provide alkaline-tolerant proteases having good thermal stability.

It is an additional object of this invention to provide a process for preparation of such alkaline proteolytic enzymes.

Other objects and advantages of the invention will become apparent from the following detailed description.

SUMMARY OF THE INVENTION

In accordance with the present invention, there is disclosed a novel Bacillus species which produces several proteolytic enzymes, at least one of which is characterized by a high degree of stability under alkaline conditions and a high degree of thermal stability. The enzymes can be produced by cultivating a novel Bacillus strain, designated GX6638, in a nutrient medium and recovering the proteases therefrom. Also disclosed are proteolytic enzymes, designated protease HS and $Q_5$, which can be isolated from the group of proteases produced by the Bacillus GX6638 strain. Protease HS exhibits especially good alkaline and thermal stability. The group of proteases produced by Bacillus strain GX6638, or protease HS alone, is useful in detergent compositions.

DETAILED DESCRIPTION OF THE INVENTION

The present invention is directed to novel enzymes possessing proteolytic activity under alkaline conditions, at least one of which exhibits a high degree of alkaline and thermal stability. The enzymes are produced by cultivating a novel alkalophic Bacillus species, designated GX6638, under suitable conditions. The proteases, and especially one protease, designated protease HS, are useful as additives to heavy duty liquid and solid detergents. As will be illustrated below, the enzymes produced by Bacillus strain GX6638 are characterized by the following properties: stability under highly alkaline conditions, stability at high temperatures, stability at high temperatures under highly alkaline conditions, stability in the presence of detergent builders and other detergent components, good storage stability in detergent formulations, activity over a broad pH range, and activity at elevated temperatures. A culture of Bacillus GX6638 has been deposited with the American Type Culture Collection, Rockville, Md., and been given accession number ATCC No. 53278.

The novel Bacillus species which produces the proteases of this invention was isolated from an alkaline soil sample taken in Maryland by means of a specific isolation procedure. The isolation was conducted at a pH within the alkaline range and at a temperature of 30°–37° C.

To obtain the enzymes of interest, the organism is cultivated under aerobic conditions in an alkaline nutrient medium containing an assimilable source of nitrogen, carbon and trace elements, and the proteolytic enzymes are recovered from the fermentation broth.

A variety of growth media can be used for cultivating Bacillus GX6638. To obtain the enzymes an aqueous fermentation medium may contain 0.1 to 1.0% yeast extract, 0.1 to 1.0% peptone, 0.1 to 0.2% inorganic phosphorous, and an assimilable carbon and energy source such as glucose, starch, or dextrins. Furthermore, certain amounts of various metal salts, such as calcium and magnesium, as well as several trace elements preferably are added.

A vigorous aeration is generally maintained during the fermentation and the pH of the medium suitably is kept between about 8.0 and about 10.5, and preferably between 9 and 10. The fermentation temperature is suitably in the range of about 30° and 40° C., and preferably is about 37° C. A productive fermentation typically is about 12 to about 24 hours in length and preferably is within the range of about 12 to 15 hours.

The enzymes can be recovered from the fermentation medium in accordance with conventional procedures. The medium first is centrifuged to remove cellular materials, then the enzymes can be precipitated by adding inorganic salts, such as ammonium sulfate, to the supernatant, and the enzymes then can be separated by ion exchange chromatography methods (see example 2). As noted above, the enzyme mixture (hereinafter designated the GX6638 proteases) has been shown to exhibit activity in alkaline media and to have a high degree of stability in highly alkaline media and at high temperatures. As illustrated in example 2, the GX6638 proteases comprise at least three separable proteases, which have been designated $Q_1$, $Q_5$, and HS. One of these proteolytic enzymes, protease HS, has been found to have especially high alkaline and thermal stability. The characteristics of proteases HS and $Q_5$ are described in detail below.

The GX6638 proteases or protease HS alone can be formulated into washing compositions. To date, a drawback in using enzymes in washing compositions has been that the enzymes have not been stable in an alkaline pH environment; consequently the pH of the washing compositions typically has been limited. This is disadvantageous, for the cleaning abilities of washing compositions increase as the pH becomes more alkaline. The GX6638 proteases, and protease HS in particular, provide a means for overcoming this problem, for, as shown below, they are stable under alkaline conditions in both aqueous and solid formulations and at high temperatures.

The proteases of this invention may be formulated into washing compositions in accordance with conventional procedures. The GX6638 proteases or protease HS is added to the composition in an amount sufficient to give the final composition a proteolytic activity of about 1,000 to about 8,000 DU/g, and preferably about 2,000 to about 4,000 DU/g. DU stands for Delft Units, and refers to a method for the determination of enzyme activity described in British Pat. No. 1,353,317.

The washing compositions to which the GX6638 proteases or protease HS is added comprise a detergent and, optionally, a detergent builder, fragrance, foam booster and coloring agent. Useful detergents include those detergents conventionally included in washing compositions, including anionic surface active agents, such as, for example, alpha olefin sulfonates, and nonionic surface active agents, such as ethoxylated alcohols. One detergent or a mixture of detergents may be included in the composition, typically in an amount ranging from about 5 to about 20 percent by weight of the final composition. Any of the optional ingredients, if desired, may be added in conventional amounts. A useful detergent builder is nitriloacetic acid.

Washing compositions containing the GX6638 proteases or protease HS also may comprise water. It has been found that these proteases are stable in compositions which comprise relatively high amounts (i.e., over 50% by weight) of water, which is economically advantageous. Current liquid washing compositions comprising enzymes typically comprise much less than 50% by weight water to prevent destabilization of the enzyme.

Properties of Protease HS

A. Temperature/Stability Relationship. For determining protease activity, the peptidase activity was determined by monitoring the increase in absorbance at 410 nm due to the release of p-nitroaniline from succinyl-L-alanyl-L-alanyl-L-prolyl-L-phenylalanyl-p-nitroanilide (sAAPFpN) (Del Mar, E. G., et al., *Anal. Biochem.* 99:316–320 [1979]). The reaction mixtures contained in a final volume of 0.7 ml, 0.001M sAAPFpN, 0.1M CAPS [3-(cyclohexylamino) propane sulfonic acid] buffer, pH 10.5 and a suitable amount of enzyme. One peptide unit of protease HS equals approximately 200 Delft Units. Thermal stabilities were determined by incubating 1–10 peptide units of protease in 1 ml of 0.1M CAPS buffer (pH 10.5) containing 0.001–0.005M ethylenediaminetetraacetic acid, disodium salt (EDTA). (The pH of the buffer was adjusted at either 50° or 60° C.) EDTA was included in buffers to chelate metal ions which enhance enzyme stability. Proteases were added to buffers preincubated at either 50° or 60° C.; aliquots were removed periodically and immediately cooled in ice-cold water, and activity determinations were made using a Gilford 2400 spectrophotometer. The time required for 50% inactivation of protease HS and Enzeco ® (a commercial protease preparation sold by Enzyme Development, Division of Biddle Sawyer Corporation, N.Y., N.Y.) was compared at 50° and 60° C. The Enzeco ® sample was purified by conventional cation exchange chromatography.

| Enzyme | Half-life (minutes): | |
|---|---|---|
| | 50° C. | 60° C. |
| Protease HS | >200 | 25 |
| Enzeco ® | 1.2 | 0.2 |

B. pH/Stability Relationship. The alkaline stability of protease HS from GX6638 and of Enzeco ® was determined by incubating 10 peptide units in 0.1 M CAPS/0.005 M EDTA buffer (pH 10.8) at 40° C. Samples were removed periodically and assayed as described before. The enzymes exhibit alkaline stability as follows:

| Enzyme | Half-life (minutes): pH 10.8 |
|---|---|
| Protease HS | >420 |
| Enzeco ® | 16 |

C. Temperature/Activity Relationship. The temperature optimum for protease HS activity was determined from initial rates of sAAPFpN hydrolysis. A Gilford Thermo-programmer 2527 was used to calibrate and maintain the reaction temperatures. At pH 10.5 (0.05M CAPS buffer), protease HS had optimal activity at 70° C.

| Temperature (°C.) | % Relative Activity |
|---|---|
| 20 | 13 |
| 30 | 30 |
| 40 | 47 |
| 50 | 64 |
| 55 | 74 |
| 60 | 87 |
| 65 | 96 |
| 70 | 100 |
| 75 | 92 |
| 80 | 64 |
| 85 | 38 |

D. pH/Activity Relationship. For determination of the pH/activity profile, azocasein (sulfanilamideazocasein, Sigma Corp., St. Louis, Mo.) was used as a substrate. Protease HS was incubated with the following buffers (0.05M) containing 0 8 mg/ml azocasein in a final volume of 0.7 milliliters: Aces, pH 7.0; Tris(hydroxymethyl)aminomethane (Tris-HCl), pH 8.0 and 8.5; Bicine, pH 9.0; $Na_2CO_3$, pH 9.5, 10 and 10.5; $Na_3PO_4$, pH 11, 11.5 and KCl/NaOH, pH 12.0. (The pH of each buffered azocasein solution was adjusted at 40° C. and 50° C.) After 10 minutes incubation at either 40° or 50° C., 0.5 milliliters 10% w/v trichloroacetic acid was added and immediately mixed, and the mixtures were stored on ice for 10 minutes. The mixtures then were centrifuged and the optical densities of the resulting supernatants were determined at 420 nm against a blank that contained either no enzyme or inactivated enzyme in the buffered azocasein solution.

The enzyme exhibits the following pH/activity profile:

| 40° C. | | | | | | | | | |
|---|---|---|---|---|---|---|---|---|---|
| pH | 7 | 8 | 8.5 | 9 | 9.5 | 10 | 10.5 | 11 | 11.5 | 12 |
| Relative Activity (%) | 80 | 92 | 92 | 96 | 100 | 84 | 92 | 76 | 60 | 52 |

| 50° C. | | | | | | | | | |
|---|---|---|---|---|---|---|---|---|---|
| pH | 7 | 8 | 8.5 | 9 | 9.5 | 10 | 10.5 | 11 | 11.5 | 12 |
| Relative Activity (%) | 43 | 89 | 92 | 100 | 100 | 97 | 84 | 52 | 40 | 24 |

Properties of Protease Q5

A. Temperature/Stability Relationship. The procedures for determining the thermal stability of protease $Q_5$ were identical to the procedures described in the section above entitled Properties of Protease HS.

| | Half-Life (minutes) | |
|---|---|---|
| Enzyme | 50° C. | 60° C. |
| Protease Q5 | 9 | 1.8 |
| Enzeco ® | 1.2 | 0.2 |

B. pH/Stability Relationship. The alkaline stability of protease $Q_5$ form GX6638 was determined by incubating 4–6 peptide units in either 0.1M CAPS/0.005 M EDTA buffer (ph 10.8) or 0.1M $Na_3PO_4$ buffer (pH 12). The incubation temperature in both cases was 40° C.

| | Half-Life (minutes) | |
|---|---|---|
| Enzyme | pH10.8 | pH12 |
| Protease Q5 | 42 | 14 |
| Enzeco ® | 16 | 1.2 |

C. Temperature/Activity Relationships. The temperature optimum for protease $Q_5$ activity was determined as described for protease HS. At pH 10.5 (0.05M CAPS buffer), protease $Q_5$ had optimal activity at 60° C.

| Temperature (°C.) | % Relative Activity |
|---|---|
| 20 | 22 |
| 25 | 30 |
| 30 | 34 |
| 35 | 41 |
| 40 | 56 |
| 45 | 59 |
| 50 | 72 |
| 55 | 84 |
| 60 | 100 |
| 65 | 88 |
| 70 | 94 |
| 75 | 81 |

D. pH/Activity Relationships. The pH/activity profile for protease $Q_5$ was determined as described for protease HS. Protease $Q_5$ exhibits the following pH/activity profile:

| 40° C. | | | | | | | |
|---|---|---|---|---|---|---|---|
| pH | 8 | 9 | 9.5 | 10 | 10.3 | 10.6 | 11.3 |
| Relative Activity (%) | 59 | 98 | 100 | 94 | 83 | 61 | 58 |

| 50° C. | | | | | | | |
|---|---|---|---|---|---|---|---|
| pH | 8 | 9.0 | 9.5 | 10.0 | 10.3 | 10.6 | 11.3 |
| Relative Activity (%) | 77 | 93 | 100 | 93 | 88 | 63 | 49 |

Further Biochemical Characteristics. The molecular weight and isoelectric point of proteases HS and $Q_5$ were determined and compared to published values for several known proteases: (1) subtilisin Carlsberg, described in Delange and Smith, *J. Biol Chem.*, 243:2134 (1968); (2) the enzyme from Bacillus strain PB92, described in U.S. Pat. No. Re. 30,602; (3) the enzyme from Bacillus sp described in U.S. Pat. No. 4,052,262; (4) the enzyme from *Bacillus firmus*, described in Dutch Patent Application No. 72.07050; and (5) the enzyme from *Bacillus sacchariticus*, described in U.S. Pat. No. 3,622,458.

| | 1 | 2 | 3 | 4 | 5 | Protease HS | Protease Q5 |
|---|---|---|---|---|---|---|---|
| Molecular Weight | 27,300 | 25,500 | 30,000 | 26,000 | 22,700 | 36,000 | 27,500 |
| Isoelectric Point | 9.3 | 10.5 | 9.4 | 11.0 | 9.3 | 4.2 | 5.2 |

TAXONOMY OF GX6638

For the taxonomic determination, use has been made of Gordon et al. ["The Genus Bacillus" U.S. Dept. of Agr. Handbook No. 427 (1973)]. The sporulation of Bacillus GX6638 was induced by cultivating cryogenically preserved cultures on potato starch carbonate medium (PSCM) agar.

Cell Morphology a. Vegetative cells: (motile) rods, ends rounded, singular in general, but also occurring in pairs during logarithmic growth.

b. Presporal forms: extensive subterminal swelling prior to microscopic observation of optically refractile spores.

c. Sporangia: subterminal swelling d. Spores: 0.6–0.8 by 1.2–1.4; ellipsoidal; optically refractile under phase contrast, swelling the sporangium. Spores are often free in late stationary phase broth cultures.

Further Characteristics a. Growth temperatures: Maximum 50°–55° C. Minimum 10°–15° C.

b. Gram reaction: Positive c. Growth on solid agar media: no growth occurs on nutrient agar buffered at pH 7.0. There is moderate growth on nutrient agar buffered at pH 7.0 supplemented with 2% NaCl and excellent growth and sporulation on nutrient agar buffered at pH 9.5 to 10.5. Growth occurred on nutrient agar supplemented with 7.5% NaCl at pH 10.0.

d. Colony morphology: Colonies formed on PSCM agar are white to beige, flat and spreading with an entire edge.

e. Biochemical reactions: No formation of a pigment on tyrosine or glucose agar at pH 10.0. Positive starch hydrolysis on potato starch agar at pH 10.0. Strong liquefaction of gelatin on gelatin/nutrient agar at pH 10.0. Clear casein digestion on milk agar at pH 10.0. Clear lipid digestion on olive oil agar at pH 10.0.

The invention disclosed and claimed herein is further illustrated by the following examples which are presented for illustrative purposes only and are not to be construed as limiting.

EXAMPLE 1

The fermentation of Bacillus GX6638 was accomplished in a medium containing 5 g/l Bactopeptone, 5 g/l Bacto-yeast extract, 10 g/l soluble potato starch, 1 g/l $K_2HPO_4$ and trace elements. The medium composition without trace elements was sterilized at a temperature of 120° C. and 15 p.s.i. for 30 minutes. After cooling, 7.1 ml of trace elements were added per liter. Trace elements were made as four separate solutions:

1. 5.4 g $FeCl_3.6H_2O$, 1.44 g $ZnSO_4.7H_2O$, 1.0 g $MnCl_2.4H_2O$, 0.25 g $CuSo_4.5H_2O$, 0.25 g $CoSO_4.6H_2O$, 0.062 g $H_3BO_3$, 13.3 ml concentrated HCl to 1 liter distilled water;
2. 61.6 g $MgSO_4.7H_2O$, 44.8 ml concentrated HCl to 1 liter distilled water;
3. 24.1 g $NaMoO_4.2H_2O$ to 1 liter distilled water, and;
4. 100 g $CaCl_2.2H_2O$ to 1 liter distilled water.

Solutions 1, 2, 3 and 4 were mixed at a ratio of 5:1:0.1:1 before addition to the composition. The final pH was adjusted to 9.5 by the addition of 20% (weight/volume) $Na_2CO_3$. The inoculation culture was prepared by inoculating the medium described above with Bacillus GX6638 and incubating at 37° C. for 18 hours on a shaking apparatus adjusted to 300 rpm.

The fermentation medium was inoculated with 1% volume of the inoculation culture. The fermentation was performed at 37° C. in stirred tank fermentors equipped with a pH controlling device and a dissolved oxygen concentration measuring device. Cell growth was monitored by periodically removing samples and measuring optical density at 660 nm. Protease activity was measured spectrophotometrically using sAAPFpN as substrate. Fermentation was continued for 12-15 hours. During this period, Bacillus GX6638 produced 17,000 peptide units of protease per liter.

Alternatively, Bacillus GX6638 was grown in 50 ml of the medium described above in 500 ml baffled Erlenmeyer flasks. Bacillus GX6638 was incubated at 37° C. for 18-24 hours on a shaking apparatus adjusted to 300 rpm.

EXAMPLE 2

The proteolytic enzymes produced by Bacillus GX6638 are separable by ion exchange chromatography. The enzymes produced in Example 1 were recovered from the fermentation broth following centrifugation to remove cellular materials. The enzymes in the supernatant fraction were concentrated by adding 582 g/l solid ammonium sulfate at 4° C. The solution was equilibrated for 30 minutes, then centrifuged at 12000×g at 4° C. for 2 hours The pellet was resuspended in 0.01M Tris-HCl buffer (pH 8.3) and dialyzed against three one liter changes of this buffer at 4° C. The conductivity of the dialysate was adjusted to two times that of a separate solution of 0.01M Tris-HCl buffer (pH 8.2) that was used to equilibrate a column packed with diethylaminoethyl (DEAE) DE52 cellulose (Whatman Chemical Separation Ltd ). The column was washed with 0.01M Tris-HCl buffer (pH 8.2), and the proteases were eluted with a linear gradient of 0–0.5M NaCl in a final volume of 1.6 liters of 0.01M Tris-HCl (pH 8 2). Fractions were collected every 15 minutes; the absorbancy of the fractions was monitored at 280 nm and protease activity was assayed as before.

Two peaks of proteolytic activity were observed. The first, designated protease $Q_1$, eluted between 0–0.1M NaCl; the second, containing protease $Q_5$ and protease HS, eluted between 0.15–0.225M NaCl. Fractions containing protease $Q_1$ were combined and fractions containing protease $Q_5$ and protease HS were combined and each pool was precipitated with 80% (weight/volume) cold acetone. Protein from the pooled protease $Q_5$ and protease HS fractions was collected by centrifugation, resuspended in 0.05M Tris-HCl (pH 8.0) and dialyzed against this buffer as described above. The dialysate was applied to a column containing QAE Sephadex A-50 (Pharmacia P-L Biochemicals, Piscataway, N.J.) previously equilibrated in 0.05M Tris-HCl (pH 8.0). The column was washed with buffer, and protease $Q_5$ and protease HS were separated with a linear gradient of 0–0.8M NaCl in 0.05M Tris-HCl (pH 8.0); fractions were collected and monitored as before. Protease $Q_5$ eluted between 0.2M and 0.25M NaCl, whereas protease HS eluted between 0.26M and 0.32M NaCl.

Proteases $Q_1$, $Q_5$ and HS are distinguishable based on molecular weight, isoelectric point, and esterase/peptidase activity ratio. (Esterase activity was determined spectrophotometrically by measuring the increase in absorbance at 340 nm of a reaction mixture containing in a final volume of 0.7 ml 10 microliters of N-carbobenzoxy-L-glycine p-nitrophenyl ester [Sigma Chemical Co.; 4.5 mg/ml in anhydrous acetonitrile], 0.67 microliters of 0.1M Aces buffer, pH 7.0, and a suitable amount of enzyme.)

|  | Molecular Weight | Isoelectric Point | Esterase/ Peptidase Ratio |
|---|---|---|---|
| Protease $Q_1$ | 22,000 | 9.5 | 0.2 |
| Protease $Q_5$ | 27,500 | 5.2 | 0.2 |
| Protease HS | 36,000 | 4.2 | 4.0 |

EXAMPLE 3

For wash tests and stability studies, the enzymes produced by GX6638 were recovered from a shake flask culture in a conventional manner. The culture broth was centrifuged and the supernatant fraction was concentrated by the addition of 582 g/l ammonium sulfate or by the addition of 80% (weight/volume) acetone. After the solution was allowed to equilibrate, the protein was recovered by centrifugation and decantation of the supernatant. The protein was redissolved in distilled water. This preparation is suitable for addition to washing compositions.

For preparation of a protease solution containing only protease HS, the GX6638 proteases were redissolved in 0.05M CAPS buffer (pH 10.5)/0.005M EDTA, rather than distilled water. The solution was heated at 60° C. for 30 minutes to inactivate other proteolytic activities while maintaining protease HS as the sole proteolytic activity. This preparation is suitable for addition to washing compositions.

EXAMPLE 4

For a standard liquid detergent formulation, the following ingredients were combined:
29.8% water
28.0% detergent blue solution (0.05%)
9.3% polyethylene glycol (PEG) 200
14.0% nitriloacetic acid (NTA), trisodium salt
7.4% sodium carbonate
0.3% fragrance
9.3% sodium alpha olefin sulfonate (AOS-90 F)

Enzeco ® protease was added to the above formulation to give a final concentration of 4,000 DU/g, and 0.6% NTA was added to adjust the pH to 10.7. Similarly, GX6638 proteases, prepared as before (Example 3), were added to the above formulation to give a final concentration of 4,000 DU/g. For this formulation, only 24.4% water was required because the GX6638 protease preparation was less concentrated than Enzeco ®. Moreover, no additional NTA was required because the final pH of the formulation was 10.6. The same formulation also was prepared using protease HS at a final concentration of 4,000 DU/g. For the HS formulation, only 17.8% water was required, and no NTA was added. The three liquid formulations were stored at 25° C. for 34 days, and enzyme activities were measured by a modified casein assay at pH 9.5 (*Methods in Enzymology*, 273–274 [1970]). The stability data are shown below.

| Day | % Activity Retention at 25° C. | | |
|---|---|---|---|
| | Protease HS | GX6638 Proteases | Enzeco ® |
| 1 | 100% | 100% | 100% |
| 6 | 79% | 76% | 58% |
| 10 | 76% | 79% | 16% |
| 13 | 81% | 74% | 12% |
| 21 | 62% | 49% | 12% |
| 27 | 53% | 45% | 10% |
| 34 | 53% | 42% | 10% |

EXAMPLE 5

The stability of the GX6638 proteases in liquid laundry detergent was determined using the commercial detergents Tide ® and Era Plus ® (both manufactured by The Proctor & Gamble Co., Cincinnati, Ohio). Both Tide ® and Era Plus ® contain enzymes, are formulated with enzyme stabilizers (see U.S. Pat. No. 4,318,818) and have a pH of 7.5. The enzymes present in these detergents were inactivated by heating at 70° C. until no enzyme activity remained. The stability determinations were carried out by introducing one-fourth volume of the enzymes of the invention, i.e., the GX6638 proteases, into three-fourths volume of each of the inactivated detergents to give a final enzyme activity of approximately 1,200 DU/ml. Active samples of Tide ® and Era Plus ® were reintroduced into their inactivated counterparts to give a comparable final enzyme activity. All samples were incubated at 60° C., sampled at time intervals, and assayed for protease activity.

| Detergent | Enzyme Source | Half-life (min) |
|---|---|---|
| Tide ® | GX6638 proteases | 540 |
| Tide ® | Tide ® | 3 |
| Era Plus ® | GX6638 proteases | 1380 |
| Era Plus ® | Era Plus ® | 21 |

EXAMPLE 6

The stability of one of the enzymes of the invention, protease HS, in liquid laundry detergent was determined using the commercial detergent, Wisk ® (Lever Brothers, Edgewater, N.J.). Wisk ® does not contain enzymes and has a pH of 10.5 in the concentrated form. This alkaline pH is not usually conducive to enzyme stability. One-fourth volume of protease HS in water was added to three-fourths volume of Wisk ® to give a final enzyme activity of approximately 1,200 DU/ml. The detergent-enzyme mixture was incubated at 60° C., sampled at time intervals and assayed for protease activity. The stability of protease HS and the commercially available protease, Enzeco ®, in Wisk ® are as follows:

| Enzyme | Half-life at 60° C. (minutes) |
|---|---|
| Protease HS | 90.0 |
| Enzeco ® | 4.5 |

EXAMPLE 7

Liquid detergent formulations were prepared with Enzeco ® enzyme and the GX6638 proteases as in Example 4. The two liquid formulations were stored at 25° C. for 29 days. The activities of the formulations were measured by the modified casein assay.

On days 1, 16 and 29, washing tests were done in a Tergotometer. The standard protocol used was 2.0 g/l formulation, 15 minutes washing time, 55° C., 1-liter washing solution, 75 rpm agitation, and a water hardness of 30 mg/l CaCO$_3$ plus 60 mg/l MgSO$_4$. Three 6"×6" pre-stained cotton swatches (fabric-EMPA [Enzyme Manufacturers Performance Assay] 116 from Test Fabrics, Inc., N.Y., N.Y.) were washed along with three unsoiled cotton swatches (EMPA 221). As a control, identical swatches were washed with the formulation without enzyme.

After the swatches were washed, they were rinsed twice with 1 liter of tap water. The swatches were dried 1 hour at 55° C., ironed, and reflectances for washed and unwashed swatches were read on a Gardner colorimeter (giving ΔL values). Cleaning ability of the enzyme was defined as the difference between the ΔL value obtained with an enzyme-containing formulation and the ΔL value obtained with the same formulation without enzyme. For ease of comparison, the cleaning ability of each enzyme at day 1 was set at 100%. The results were as follows:

| Enzyme | % Cleaning Ability | | |
|---|---|---|---|
| | Day 1 | Day 16 | Day 29 |
| Enzeco ® | 100 | 3 | 0 |
| GX6638 proteases | 100 | 35 | 31 |

EXAMPLE 8

For a standard solid detergent formulation, the following ingredients were combined at 55° C.:

26.7% detergent blue solution (0.05%)
8.1% water
26.5% PEG 8,000
11.0% Neodol 45-7 (commercially available ethoxylated alcohol detergent)
7.5% AOS-90F
8.6% sodium sulfate
8.4% NTA, trisodium salt
0.7% methyl cellulose
0.3% fragrance
0.5% cocamide DEA (foam booster)

Enzeco ® protease was added to the above formulation to give a final concentration of 4,000 DU/g, and the pH was adjusted to 8.8. Similarly, GX6638 proteases, prepared as before (Example 3), were added to the above formulation to give a final concentration of 4,000 DU/g and the pH adjusted to 8.4. Enzyme activities were measured by a modified casein assay (Example 4).

| Enzyme | pH | % Retention of Activity After 48 Hours @ 55° C. |
|---|---|---|
| Enzeco ® | 8.8 | 5 |
| GX6638 proteases | 8.4 | 70 |

EXAMPLE 9

Enzeco ® protease was diluted with water to 47,400 DU/g and mixed with PEG 8000 at 55° C. at a ratio of 84% enzyme and 16% PEG. This mixture was rapidly cooled until it hardened and then ground into a powder with a mortar and pestle. The activity of the resulting product was 32,680 DU/g. It then was added to Arm & Hammer ® (Church & Dwight Co., Inc., Princeton, N.J.) laundry powder at a ratio of 12% Enzeco ® protease mixture and 88% Arm & Hammer ® powder and mixed with a mortar and pestle.

The GX6638 proteases were concentrated as before (Example 3) to 47,400 DU/g and was mixed with PEG 8,000 by the same procedure as described above for Enzeco ®. The activity of the resulting mixture was 34,040 DU/g. It was added to Arm & Hammer ® powder at concentrations of 12% GX6638 proteases to 88% Arm & Hammer ® powder. When dissolved in water, the activity of both the Enzeco ® and GX6638 protease detergent mixtures was 4,000 DU/g, and each had a pH of 11.

Each powder was stored at 25° C. for 66 days, and the proteolytic activities were assayed after 1, 14 and 66 days using the modified casein assay (Example 4). The results were as follows:

| Storage Time (Days) | % Activity Retained | |
|---|---|---|
| | Enzeco ® Formulation | GX6638 Formulation |
| 1 | 100 | 100 |
| 14 | 93 | 98 |
| 66 | 67 | 89 |

We claim:

1. A process for the preparation of one or more enzymes having proteolytic activity in alkaline media and exhibiting high alkaline and thermal stability which comprises cultivating Bacillus strain GX6638 or an alkaline protease producing mutant or variant thereof in a fermentation medium and recovering therefrom the enzyme or enzymes produced by said Bacillus strain.

2. The process of claim 1, wherein the fermentation medium comprises carbon, nitrogen, magnesium salts, calcium salts and trace elements.

3. The process of claim 1, wherein following cultivation of the Bacillus strain the fermentation medium is centrifuged to remove cellular material, then the enzyme or enzymes is concentrated in the supernatant, precipitated from said supernatant and recovered.

4. A member of the group consisting of Bacillus novel species GX6638 and its proteolytic enzyme producing mutants and variants.

5. A biologically pure culture of Bacillus strain GX6638 or an alkaline protease producing mutant or variant thereof.

6. A substantially pure mixture of enzymes produced by cultivation. Bacillus strain GX6638 or an alkaline protease producing mutant or variant thereof, said mixture comprising at least three separate enzymes having proteolytic activity, wherein said three enzymes have molecular weights of about 22,000, about 27,500 and about 36,000, and isoelectric points of about 9.5, 5.2 and 4.2, respectively.

7. A substantially pure alkaline protease characterized by the following properties:
    (a) a molecular weight of about 27,500;
    (b) an isoelectric point of about 5.2;
    (c) an optimal proteolytic activity at a pH of about 9.5 at a temperature of 40°–50° C., said optimal activity measured in an assay wherein sulfanilamide azocasein was used as the substrate;
    (d) an optimal activity at 60° C. at a pH of about 10.5, said optimal activity measured against a synthetic peptide having the sequence succinyl-L-alanyl-L-alanyl-L-prolyl-L-phenylalanyl-p-nitroanilide;
    (e) a half-life of about 9 minutes at 50° C. and a pH of about 10.5;
    (f) a half-life of about 1.8 minutes at 60° C. and a pH of about 10.5;
    (g) a half-life of about 14 minutes at 40° C. and a pH of about 12; and
    (h) a half-life of about 42 minutes at 40° C. and a pH of about 10.8.

8. A substantially pure alkaline protease characterized by the following properties:
    (a) a molecular weight of about 36,000;
    (b) an isoelectric point of about 4.2;
    (c) an optimal proteolytic activity at a pH of about 9.5 at a temperature of about 40°–50° C., said optimal activity measured in an assay wherein sulfanilamideazocasein was used as the substrate;
    (d) an optimal activity at 70° C. at a pH of about 10.5, said optimal activity measured against a synthetic peptide having the sequence succinyl-L-alanyl-L-alanyl-L-prolyl-L-phenylalanyl-p-nitroanilide;
    (e) a half-life of at least 200 minutes at 50° C. at a pH of 10.5;
    (f) a half-life of about 25 minutes at 60° C. and a pH of 10.5; and
    (g) a half-life of at least 420 minutes at a pH of 10.8, and a temperature of 40° C.

9. A washing composition containing an effective amount of the enzyme mixture of claim 6 having high alkaline and thermal stability.

10. A washing composition containing an effective amount of the enzyme of claim 9 having high alkaline and thermal stability.

11. The washing composition of claim 9 or 10, which further comprises a detergent.

12. The washing composition of claim 11, which further comprises a detergent builder, foam booster, fragrance or coloring agent.

13. The washing composition of claim 11 wherein said detergent is an ethoxylated alcohol or a linear alkyl sulfonate.

14. The washing composition of claim 12 wherein the detergent builder is nitriloacetate, trisodium salt.

* * * * *